United States Patent [19]

Wegner et al.

[11] Patent Number: 5,159,117
[45] Date of Patent: Oct. 27, 1992

[54] PREPARATION OF α,α-DIALKOXY KETONES

[75] Inventors: Guenter Wegner, Speyer; Stefan Karbach, Neustadt; Hubert Smuda, Heidelberg; Eckhard Hickmann, Dannstadt-Schauernheim; Reiner Kober; Rainer Seele, both of Fussgoenheim; Thomas Zierke, Boehl-Iggelheim, all of Fed. Rep. of Germany

[73] Assignee: BASF Aktiengesellschaft, Ludwigshafen, Fed. Rep. of Germany

[21] Appl. No.: 747,575

[22] Filed: Aug. 20, 1991

[30] Foreign Application Priority Data

Aug. 24, 1990 [DE] Fed. Rep. of Germany ....... 4026788

[51] Int. Cl.$^5$ .................................................. C07C 41/56
[52] U.S. Cl. .................................. 568/312; 568/315; 568/343; 568/347; 568/388; 568/391; 568/433; 568/458; 549/370; 549/375; 549/448; 549/454
[58] Field of Search ............... 568/391, 388, 312, 315, 568/391, 343, 347, 388, 433, 458; 549/370, 375, 448, 454

[56] References Cited

FOREIGN PATENT DOCUMENTS 0122479 10/1984 European Pat. Off. ............ 568/388
0222217 10/1986 European Pat. Off. ............ 568/388
1252193 10/1967 Fed. Rep. of Germany ...... 568/388
3539629 5/1987 Fed. Rep. of Germany ...... 568/388

OTHER PUBLICATIONS

Gordeeva et al, Chem. Abst., vol. 108, #112, 116x (1988).
Gordeeva et al, Zh. Org. Khim, vol. 23, pp. 1047–1052 (1987).
Gordeeva et al, Zh. Org. Khim, vol. 22, pp. 1075–1078 (1986).

Primary Examiner—James H. Reamer
Attorney, Agent, or Firm—Keil & Weinkauf

[57] ABSTRACT

A process for preparing α,α-dialkoxy ketones of the formula I

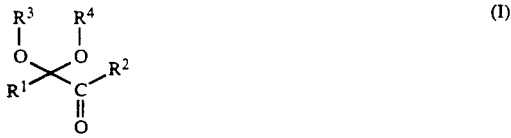

where
R$^1$ and R$^2$ are each, independently of one another, hydrogen, C$_1$–C$_{20}$-alkyl, C$_3$–C$_{20}$-cycloalkyl, C$_4$–C$_{30}$-cycloalkylakyl, C$_9$–C$_{30}$-alkylcycloalkyl, unsubstituted or C$_1$–C$_8$-alkyl, C$_1$–C$_8$-alkoxy-, halogen-, C$_1$–C$_4$-haloalkyl-, C$_1$–C$_4$-haloalkoxy-, phenyl-, phenoxy-, halophenyl-, halophenoxy- and/or cyano-substituted aryl, C$_7$–C$_{20}$-aralkyl or heterocyclyl,
R$^2$ is also

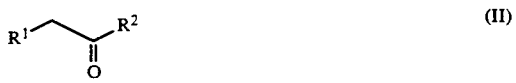

R$^3$ and R$^4$ are each, independently of one another, C$_1$–C$_{20}$-alkyl, C$_3$–C$_{20}$-cycloalkyl, aryl, C$_7$–C$_{20}$-arylalkyl, or together are an unsubstituted or C$_{1-C4}$-alkyl- substituted C$_2$–C$_7$-alkylene chain and
R$^5$ is R$^1$ or together with R$^1$ is an unsubstituted or C$_1$–C$_4$-alkyl-substituted C$_2$–C$_7$-alkylene chain,
which entails reacting ketones or aldehydes of the formula II

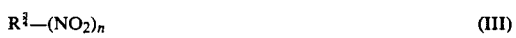

with nitrites of the formula III $$R^3{-}(NO_2)_n \qquad (III)$$

where n is 1 or 2, and n is 2 when R$^3$ and R$^4$ together are an unsubstituted or C$_1$–C$_4$-alkyl-substituted C$_2$–C$_7$-alkylene chain, with the proviso that the nitrite radicals are located at the termini, or with a mixture of alcohol of the formula IV

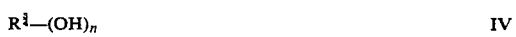

where n is 1 or 2, and n is 2 when R$^3$ and R$^4$ together are an unsubstituted or C$_1$–C$_4$-alkyl-substituted C$_2$–C$_7$-alkylene chain, with the proviso that the hydroxyl group is located at the terminus, and dinitrogen trioxide in a molar ratio of 2:1 in the presence of an acid catalyst at from 0° to 170° C.

1 Claim, No Drawings

PREPARATION OF α,α-DIALKOXY KETONES

The present invention relates to an improved process for preparing α,α-dialkoxy ketones by acid-catalyzed reaction of ketones or aldehydes with alkyl nitrites or a mixture of an alcohol and dinitrogen trioxide in the molar ratio 2:1.

EP-A-222 217 discloses the preparation of dialkoxyacetophenones in alcohols as both reactant and solvent. The yields and purities of the products from this process were in need of improvement. It was particularly desirable to avoid the formation of acetals which are difficult to remove and were unavoidable in this procedure.

It is an object of the present invention to remedy the abovementioned disadvantages.

We have found that this object is achieved by a novel and improved process for preparing α,α-dialkoxy ketones of the formula I

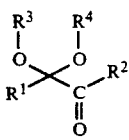   (I)

where
$R^1$ and $R^2$ are each, independently of one another, hydrogen, $C_1$–$C_{20}$-alkyl, $C_3$–$C_{20}$-cycloalkyl, $C_4$–$C_{30}$-cycloalkylalkyl, $C_9$–$C_{30}$-alkylcycloalkyl, unsubstituted or $C_1$–$C_8$-alkyl-, $C_1$–$C_8$-alkoxy-, halogen-, -$C_1$–$C_4$-haloalkyl-, $C_1$–$C_4$-haloalkoxy-, phenyl-, phenoxy-, halophenyl-, halophenoxy- and/or cyano-substituted aryl, $C_7$–$C_{20}$-aralkyl or heterocyclyl,
is also

$R^3$ and $R^4$ are each, independently of one another, $C_1$–$C_{20}$-alkyl, $C_3$–$C_{20}$-cycloalkyl, aryl, $C_7$–$C_{20}$-aralkyl, or together are an unsubstituted or $C_1$–$C_4$-alkyl-substituted $C_2$–$C_7$-alkylene chain and
$R^5$ is $R^1$ or together with $R^1$ is an unsubstituted or $C_1$–$C_4$-alkyl-substituted $C_2$–$C_7$-alkylene chain,
which comprises reacting ketones or aldehydes of the formula II

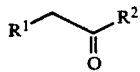   (II)

with nitrites of the formula III $R^3\text{—}(NO_2)_n$   (III)

where n is 1 or 2, and n is 2 when $R^3$ and $R^4$ together are an unsubstituted or $C_1$–$C_4$-alkyl-substituted $C_2$–$C_7$-alkylene chain, with the proviso that the nitrite radicals are located at the termini, or with a mixture of alcohol of the formula IV $R^3\text{—}(OH)_n$   IV where n is 1 or 2, and n is 2 when $R^3$ and $R^4$ together are an unsubstituted or $C_1$–$C_4$-alkyl-substituted $C_2$–$C_7$-alkylene chain, with the proviso that the hydroxyl group is located at the terminus, and dinitrogen trioxide in a molar ratio of 2:1 in the presence of an acid catalyst at from 0° to 170° C.

The process according to the invention can be carried out in the following way:

the ketones or aldehydes of the formula II are reacted in the presence or absence of an inert solvent with alkyl nitrites or a mixture of an alcohol and dinitrogen trioxide in the molar ratio 2:1 in the absence of an excess of alcohol in the presence of an acid catalyst at from 0° to 170° C., preferably 20° to 140° C., particularly preferably 30° to 120° C.

Suitable and preferred solvents are unsubstituted or substituted aromatic compounds such as toluene, xylenes, mesitylene, chlorobenzene, fluorobenzene or ethylbenzene, and aliphatic compounds such as heptane, hexane, cyclohexane, octane, isooctane, petroleum ether or naphtha, or haloaliphatic compounds such as chloroform, dichloromethane, perchloroethylene, fluorochloromethanes, fluorochloroethanes and mixtures of these solvents.

The alkyl nitrites or alcohols provide the radicals $R^3$ and $R^4$ in the final products. Preferably employed are methyl nitrite, ethyl nitrite, isopropyl nitrite, n-propyl nitrite, n-butyl nitrite, 2,2-dimethyl-1,3-propylene dinitrite and glycol dinitrite, and the analogous alcohols with dinitrogen trioxide in the stoichiometric ratio 2:1 per hydroxyl group.

Acids are used as catalysts, preferably HCl, HBr, toluenesulfonic acid, methanesulfonic acid, sulfuric acid, phosphoric acid, acetic acid, trifluoroacetic acid and tetrafluoroboric acid. From 0.05 to 1 mole of acid catalyst is employed per mole of ketone or aldehyde.

The reaction can be carried out at from 020 to 170° C., preferably at the boiling point of the solvent, but generally at from 30° to 90° C. The reaction can also be carried out under elevated pressure if the solvents are appropriate or the reactants are gaseous under atmospheric pressure.

The process according to the invention can be carried out either batchwise or continuously.

After the reaction is complete, which generally takes from 1 to 10 hours, the pH is adjusted to from 7 to 10 by addition of bases (e.g. sodium hydroxide, potassium hydroxide, potassium carbonate, calcium oxide or alcoholates), which also decomposes excess nitrite.

The neutralized solution is washed and fractionally distilled to give the required products.

$R^1$, $R^2$, $R^3$, $R^4$ and $R^5$ in the compounds I, II, III and IV have the following meanings:
$R^1$ and $R^2$, independently of one another,
  hydrogen
  $C_1$–$C_{20}$-alkyl, preferably $C_1$–$C_8$-alkyl, particularly preferably $C_1$–$C_4$-alkyl such as methyl, ethyl, n-propyl, isopropyl, n-butyl, isobutyl, sec-butyl and tert-butyl,
  $C_3$–$C_{20}$-cycloalkyl, preferably $C_3$–$C_8$-cycloalkyl such as cyclopropyl, cyclobutyl, cyclopentyl, cyclohexyl, cycloheptyl and cyclooctyl, particularly preferably cyclopentyl and cyclohexyl,
  $C_4$–$C_{30}$-cycloalkylalkyl, preferably $C_4$–$C_{20}$-cycloalkylalkyl such as cyclopentylmethyl, cyclohexylmethyl, 1-cyclohexylethyl and 2-cyclohexylethyl, $C_4$-$C_{30}$-alkylcycloalkyl, preferably $C_4$-$C_{20}$-alkylcycloalkyl such as 4-methylcyclohexyl, 4-ethylcyclohexyl and 2-methylcyclohexyl, aryl such as phenyl, 1-naphthyl and 2-naphthyl, preferably phenyl, aryl mono- to trisubstituted by $C_1$-$C_8$-alkyl, preferably phenyl mono- to trisubstituted by $C_1$-$C_4$-alkyl, such as 2-methylphenyl, 4-methylphenyl, 2-ethylphenyl, 4-ethylphenyl, 3-methylphenyl, 2,4-dimethylphenyl, 3,4-dimethylphenyl and 3,4,5-trimethylphenyl, aryl mono- to trisubstituted by $C_1$-$C_8$-alkoxy, preferably phenyl mono- to trisubstituted by $C_1$-$C_4$-alkoxy, such as 2-methoxyphenyl, 2-ethoxyphenyl, 3-methoxyphenyl, 4-methoxyphenyl, 3-ethoxyphenyl, 4-ethoxyphenyl, 3,4-dimethoxyphenyl and 3,4,5-trimethoxyphenyl, aryl mono- to trisubstituted by $C_1$-$C_4$-haloalkyl, preferably phenyl mono- to trisubstituted by $C_1$-$C_2$-fluoro- or chloroalkyl, particularly preferably phenyl mono- to trisubstituted by trifluoromethyl or trichloromethyl, such as 4-trifluoromethylphenyl and 4-trichloromethylphenyl, aryl mono- to trisubstituted by $C_1$-$C_4$-haloalkoxy, preferably phenyl mono- to trisubstituted by $C_1$-$C_2$-fluoro- or chloroalkoxy, particularly preferably phenyl mono- to trisubstituted by trifluoromethoxy or trichloromethoxy, such as trifluoromethoxyphenyl, aryl mono- to trisubstituted by halogen, preferably phenyl mono- to trisubstituted by fluorine or chlorine, such as 4-chlorophenyl, 3,4-dichlorophenyl, 4-bromophenyl, 4-fluorophenyl and 4-fluoro-3-chlorophenyl, aryl mono- to trisubstituted by halophenyl, preferably phenyl mono- to trisubstituted by fluoro- and/or chlorophenyl, such as 4-chlorophenylphenyl, aryl mono- to trisubstituted by halophenoxy, preferably phenyl mono- to trisubstituted by fluoro- and/or chlorophenoxy, such as 4-fluorophenoxyphenyl, aryl mono- to trisubstituted by cyano, preferably phenyl mono- to trisubstituted by cyano, such as 2-cyanophenyl, 3-cyanophenyl and 4-cyanophenyl, $C_7$-$C_{20}$-arylalkyl, preferably $C_7$-$C_{12}$-arylalkyl such as benzyl, phenylethyl, phenylpropyl and phenylisopropyl, $C_7$-$C_{20}$-arylalkyl mono- to trisubstituted by halogen in the aryl moiety, preferably $C_7$-$C_{10}$-phenylalkyl mono- to trisubstituted by fluorine or chlorine in the phenyl moiety, such as 4-fluorobenzyl, 4-chlorobenzyl, 2,4-dichlorobenzyl and 3,4-dichlorobenzyl, $C_7$-$C_{20}$-arylalkyl mono- to trisubstituted by $C_1$-$C_8$-alkyl in the aryl moiety, preferably $C_7$-$C_{10}$-phenylalkyl mono- to trisubstituted by $C_1$-$C_4$-alkyl in the phenyl moiety, particularly preferably $C_7$-$C_{10}$-phenylalkyl mono- to trisubstituted by $C_1$-$C_2$-alkyl in the phenyl moiety, such as 4-methylbenzyl, 4-ethylbenzyl and 4-methylphenethyl, $C_7$-$C_{20}$-arylalkyl mono- to trisubstituted by $C_1$-$C_8$-alkoxy in the aryl moiety, preferably $C_7$-$C_{10}$-phenylalkylmono- to trisubstituted by $C_1$-$C_4$-alkoxy in the phenyl moiety, particularly preferably $C_7$-$C_{10}$-phenylalkyl mono- to trisubstituted by $C_1$-$C_2$-alkoxy in the phenyl moiety, such as 4-methoxybenzyl, 4-ethoxybenzyl and 4-methoxyphenethyl, $C_7$-$C_{20}$-arylalkyl mono- to trisubstituted by $C_1$-$C_4$-haloalkyl in the aryl moiety, preferably $C_7$-$C_{10}$-phenylalkyl mono- to trisubstituted by $C_1$-$C_2$-fluoro- or chloroalkyl in the phenyl moiety, particularly preferably $C_7$-$C_{10}$-phenylalkyl mono- to trisubstituted by trifluoromethyl or trichloromethyl in the phenyl moiety, such as 4-trifluoromethylbenzyl and 4-trichloromethylbenzyl, $C_7$-$C_{20}$-arylalkyl mono- to trisubstituted by $C_1$-$C_4$-haloalkoxy in the aryl moiety, preferably $C_7$-$C_{10}$-phenylalkyl mono- to trisubstituted by $C_1$-$C_2$-haloalkoxy in the phenyl moiety, particularly preferably $C_7$-$C_{10}$-phenylalkyl mono- to trisubstituted by trifluoromethoxy or trichloromethoxy, such as 4-trifluoromethoxybenzyl and 4-trichloromethoxybenzyl, $C_7$-$C_{20}$-arylalkyl mono- to trisubstituted by halophenyl, preferably $C_7$-$C_{12}$-phenylalkyl mono- to trisubstituted by fluoro- and/or chlorophenyl, such as 4-chlorophenylphenethyl and 4-fluorophenylphenethyl, $C_7$-$C_{20}$-arylalkyl mono- to trisubstituted by halophenoxy, preferably $C_7$-$C_{12}$-phenylalkyl mono- to trisubstituted by fluoro- and/or chlorophenoxy, such as 2-chlorophenoxyphenethyl and 4-chlorophenoxyphenethyl, $C_7$-$C_{20}$-arylalkyl mono- to trisubstituted by cyano, preferably $C_7$-$C_{12}$-phenylalkyl mono- to trisubstituted by cyano, such as 2-cyanobenzyl, 4-cyanobenzyl, 2-cyanophenethyl and 4-cyanophenethyl, phenyl substituted by one, two or three phenyl groups such as 2-phenylphenyl, 3-phenylphenyl, 4-phenylphenyl and 3,4-diphenylphenyl, phenyl substituted by one, two or three phenoxy groups, such as 4-phenoxyphenyl and 2-phenoxyphenyl, phenyl di- or trisubstituted by halogen and $C_1$-$C_4$-alkyl, such as 2-methyl-4-chlorophenyl and 3-methyl-4-fluorophenyl, phenyl di- or trisubstituted by halogen and $C_1$-$C_4$-alkoxy, such as 3-chloro-4-methoxyphenyl, phenyl di- or trisubstituted by halogen and $C_1$-$C_4$-haloalkyl, such as 2-chloro-4-trifluoromethylphenyl, phenyl di- or trisubstituted by halogen and phenoxy, such as 3-chloro-4-phenoxyphenyl, phenyl di- or trisubstituted by $C_1$-$C_4$-alkyl and $C_1$-$C_4$-alkoxy, such as 2-methyl-4-methoxyphenyl, phenyl di- or trisubstituted by $C_1$-$C_4$-alkyl and $C_1$-$C_4$-haloalkyl, such as 3-methyl-4-trichloromethylphenyl, phenyl di- or trisubstituted by $C_1$-$C_4$-alkyl and phenoxy, such as 2-methyl-4-phenoxyphenyl, phenyl di- or trisubstituted by $C_1$-$C_4$-alkoxy and $C_1$-$C_4$-haloalkyl, such as 3-trifluoromethyl-4-methoxyphenyl, phenyl di- or trisubstituted by $C_1$-$C_4$-alkoxy and phenoxy, such as 3-methoxy-4-phenoxyphenyl, phenyl di- or trisubstituted by $C_1$-$C_4$-haloalkyl and phenoxy, such as 3-trifluoromethyl-4-phenoxyphenyl, phenyl trisubstituted by halogen, $C_1$–$C_4$-alkyl and $C_1$–$C_4$-alkoxy, such as 2-chloro-3-tert-butyl-4-methoxyphenyl, phenyl trisubstituted by halogen, $C_1$–$C_4$-alkyl and $C_1$–$C_4$-haloalkyl, such as 2-methyl-3-chloro-4-trifluoromethylphenyl, phenyl trisubstituted by halogen, $C_1$–$C_4$-alkyl and phenoxy, such as 4-chloro-2-ethyl-3-phenoxyphenyl, phenyl trisubstituted by halogen, $C_1$–$C_4$-alkoxy and $C_1$–$C_4$-haloalkyl, such as 3-chloro-4-methoxy-3-trifluoromethylphenyl, phenyl trisubstituted by halogen, $C_1$–$C_4$-alkoxy and phenoxy, such as 2-fluoro-4-ethoxy-3-phenoxyphenyl, phenyl trisubstituted by halogen, $C_1$–$C_4$-haloalkyl and phenoxy, such as 4-fluoro-3-trifluoromethyl-2-phenoxyphenyl, phenyl trisubstituted by $C_1$–$C_4$-alkyl, $C_1$–$C_4$-alkoxy and $C_1$–$C_4$-haloalkyl, such as 4-methyl-3-methoxy-2-trichloromethylphenyl, phenyl trisubstituted by $C_1$–$C_4$-alkyl, $C_1$–$C_4$-alkoxy and phenoxy, such as 4-methyl-3-ethoxy-2-phenoxyphenyl, phenyl trisubstituted by $C_1$–$C_4$-alkyl, $C_1$–$C_4$-haloalkyl and phenoxy, such as 2-methyl-4-trifluoromethyl-3-phenoxyphenyl, phenyl trisubstituted by $C_1$–$C_4$-alkoxy, $C_1$–$C_4$-haloalkyl and phenoxy, such as 4-methoxy-2-trichloromethyl-3-phenoxyphenyl, $R^2$ additionally

$R^3$ and $R^4$, independently of one another $C_1$–$C_{20}$-alkyl, preferably $C_1$–$C_8$-alkyl, particularly preferably $C_1$–$C_4$-alkyl such as methyl, ethyl, n-propyl, isopropyl, n-butyl, isobutyl, sec-butyl and tert-butyl, $C_3$–$C_{20}$-cycloalkyl, preferably $C_3$–$C_8$-cycloalkyl such as cyclopropyl, cyclobutyl, cyclopentyl, cyclohexyl, cycloheptyl and cyclooctyl, particularly preferably cyclopentyl and cyclohexyl, aryl such as phenyl, 1-naphthyl and 2-naphthyl, preferably phenyl, $C_7$–$C_{20}$-arylalkyl, preferably $C_7$–$C_{12}$-arylalkyl such as benzyl, phenethyl, phenylpropyl and phenylisopropyl, together an unsubstituted or $C_1$–$C_4$-alkyl-substituted $C_2$–$C_7$-alkylene chain such as $(CH_2)_2$, $(CH_3)_3$, $(CH_2)_4$, $(CH_2)_5$, $(CH_2)_6$, $(CH_2)_7$, $CH_2$—$CH(CH_3)$, $CH(CH_3)$—$CH(CH_3)$, $CH_2$—$C(CH_3)_2$, $CH_2$—$CH_2$—$CH(CH_3)$, $CH_2$—$CH(CH_3)$—$CH_2$, $CH_2$—$C(CH_3)_2$—$CH_2$, $(CH_2)_3$—$CH(CH_3)$ and $(CH_2)_2$—$CH(CH_3)$—$CH_2$, preferably $(CH_2)_2$, $(CH_2)_3$, $(CH_2)_4$, $(CH_2)_5$, $(CH_2)_6$, $(CH_2)_7$ and $CH_2$—$C(CH_3)_2$ $R^5$ all the meanings of $R^1$ together with $R^1$ an unsubstituted or $C_1$–$C_4$-alkyl-substituted $C_2$–$C_7$-alkylene chain such as $(CH_2)_2$, $(CH_3)_3$, $(CH_2)_4$, $(CH_2)_5$, $(CH_2)_6$, $(CH_2)_7$, $CH_2$—$C(CH_3)_2$—$CH_2$, $CH_2$—$CH(CH_3)$, $CH(CH_3)$—$CH(CH_3)$, $CH_2$—$C(CH_3)_2$, $CH_2$—$CH_2$—$CH(CH_3)$, $CH_2$—$CH(CH_3)$—$CH_2$, $CH_2$—$C(CH_3)_2$—$CH_2$, $(CH_2)_3$—$CH(CH_3)$ and $(CH_2)_2$—$CH(CH_3)$—$CH_2$, preferably $(CH_2)_2$, $(CH_2)_4$, $(CH_2)_4$, $(CH_2)_5$, $(CH_2)_6$, $(CH_2)_7$ and $CH_2$—$C(CH_3)_2$.

The α,α-dialkoxy ketones which can be prepared by the novel process are valuable intermediates for synthesizing crop protection agents and pharmaceuticals (EP-A 94 564, EP-A 38 196 038, EP-A-196 583, DE-A 30 47 726 and DE-A 31 50 204).

EXAMPLES

EXAMPLE 1

Preparation of α,α-dimethoxyacetophenone 15 g of gaseous HCl are passed into 61 g (0.5 mol) of acetophenone in 750 ml of toluene, and the mixture is heated to 40°–45° C., and then 1.2 mol of methyl nitrite are passed in over the course of 3–4 hours. The reaction solution is made alkaline with 20% strength sodium hydroxide solution, and the organic phase is separated off and washed. Distillation results in 85% of pure α,α-dimethoxyacetophenone.

The compounds listed in the following table have been or can be prepared in a similar manner to Example 1.

TABLE

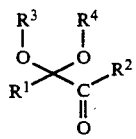

| Ex. No. | $R^1$ | $R^2$ | $R^3$ | $R^4$ | B.p. | 250 MHz $^1$H-NMR in CDCl$_3$ δ [ppm] | Yield [%] |
|---|---|---|---|---|---|---|---|
| 1 | H | $C_6H_5$ | $CH_3$ | $CH_3$ | | 3.47(6H, OCH$_3$), 5.22(1H, CH), 7.45, 7.57, 8.11(5H, Ar—H) | 85 |
| 2 | H | 2-$C_4H_3S$ | $CH_3$ | $CH_3$ | | 3.49(6H, OCH$_3$), 5.08(1H, CH), 7.14, 7.69, 8.02(3H, Het-H) | 75 |
| 3 | H | 3-$C_4H_3S$ | $CH_3$ | $CH_3$ | | 3.47(6H, OCH$_3$), 5.03(1H, CH), 7.30, 7.64, 8.39(3H, Het-H) | 78 |
| 4 | H | $C_4H_3O$ | $CH_3$ | $CH_3$ | | | |
| 5 | H | 4-Cl—$C_6H_4$ | $CH_3$ | $CH_3$ | | | |
| 6 | H | 4-Br—$C_6H_4$ | $CH_3$ | $CH_3$ | | | |
| 7 | H | 4-F—$C_6H_4$ | $CH_3$ | $CH_3$ | 60–75° C./ 0.3 mbar | 3.47(6H, OCH$_3$). 5.14(1H, CH), 7.11, 8.17(4H, Ar—H) | 85 |
| 8 | H | 2-F—$C_6H_4$ | $CH_3$ | $CH_3$ | | | |
| 9 | H | 2,4-$Cl_2$—$C_6H_3$ | $CH_3$ | $CH_3$ | | | |
| 10 | H | 2,4-$F_2$—$C_6H_3$ | $CH_3$ | $CH_3$ | | | |

TABLE-continued

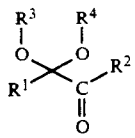

| Ex. No. | R¹ | R² | R³ | R⁴ | B.p. | 250 MHz ¹H-NMR in CDCl₃ δ [ppm] | Yield [%] |
|---|---|---|---|---|---|---|---|
| 11 | H | 4-CH₃—C₆H₃ | CH₃ | CH₃ | | | |
| 12 | H | 4-CF₃—C₆H₄ | CH₃ | CH₃ | 75–78° C./ 0.3 mbar | 3.50(6H, OCH₃), 5.12(1H, CH), 7.11, 8.17(4H, Ar—H) | 82 |
| 13 | H | 3-CF₃—C₆H₄ | CH₃ | CH₃ | | 1.20(9H, CH₃), 3.39(6H, OCH₃), 4.96(1H, CH) | 78 |
| 14 | H | (CH₃)₃C | CH₃ | CH₃ | | | |
| 15 | H | C₆H₅ | C₅H₁₁ | C₅H₁₁ | | | |
| 16 | H | 4-Cl—C₆H₄ | C₅H₁₁ | C₅H₁₁ | | | |
| 17 | H | 4-Br—C₆H₄ | C₅H₁₁ | C₅H₁₁ | | | |
| 18 | H | 4-F—C₆H₄ | C₅H₁₁ | C₅H₁₁ | | | |
| 19 | H | 2-F—C₆H₄ | C₅H₁₁ | C₅H₁₁ | | | |
| 20 | H | 2,4-Cl₂—C₆H₃ | C₅H₁₁ | C₅H₁₁ | | | |
| 21 | H | 2,4-F₂—C₆H₃ | C₅H₁₁ | C₅H₁₁ | | | |
| 22 | H | 4-CH₃—C₆H₄ | C₅H₁₁ | C₅H₁₁ | | | |
| 23 | H | 4-CF₃—C₆H₄ | C₅H₁₁ | C₅H₁₁ | | | |
| 24 | H | 3-CF₃—C₆H₄ | C₅H₁₁ | C₅H₁₁ | | | |
| 25 | H | C₆H₅ | —CH₂—C(CH₃)₂ | —CH₂— | | | |
| 26 | H | 4-Cl—C₆H₄ | —CH₂—C(CH₃)₂ | —CH₂— | | | |
| 27 | H | 4-Br—C₆H₄ | —CH₂—C(CH₃)₂ | —CH₂— | | | |
| 28 | H | 4-F—C₆H₄ | —CH₂—C(CH₃)₂ | —CH₂— | | | |
| 29 | H | 2-F—C₆H₄ | —CH₂—C(CH₃)₂ | —CH₂— | | | |
| 30 | H | 2,4-Cl₂—C₆H₃ | —CH₂—C(CH₃)₂ | —CH₂— | | | |
| 31 | H | 2,4-F₂—C₆H₃ | —CH₂—C(CH₃)₂ | —CH₂— | | | |
| 32 | H | 4-CH₃—C₆H₄ | —CH₂—C(CH₃)₂ | —CH₂— | | | |
| 33 | H | 4-CF₃—C₆H₄ | —CH₂—C(CH₃)₂ | —CH₂— | | | |
| 34 | H | 3-CF₃—C₆H₄ | —CH₂—C(CH₃)₂ | —CH₂— | | | |
| 35 | H | 4-Cl—C₆H₄ | —CH₂—CH₂ | | | | |
| 36 | H | 4-Br—C₆H₄ | —CH₂—CH₂— | | | | |
| 37 | H | 4-F—C₈H₄ | —CH₂—CH₂— | | | | |
| 38 | H | 2-F—C₆H₄ | —CH₂—CH₂ | | | | |
| 39 | H | 2,4-Cl₂—C₆H₃ | —CH₂—CH₂— | | | | |
| 40 | H | 2,4-F₂—C₆H₃ | —CH₂—CH₂— | | | | |
| 41 | H | 4-CH₃—C₆H₄ | —CH₂—CH₂— | | | | |
| 42 | H | 4-CF₃—C₆H₄ | —CH₂—CH₂— | | | | |
| 43 | H | 3-CF₃—C₆H₄ | —CH₂—CH₂— | | | | |
| 44 | C₆H₅ | CH₃ | CH₃ | CH₃ | | | |
| 45 | 4-Cl—C₆H₄ | CH₃ | CH₃ | CH₃ | | | |
| 46 | 4-Br—C₆H₄ | CH₃ | CH₃ | CH₃ | | | |
| 47 | 4-F—C₆H₄ | CH₃ | CH₃ | CH₃ | | | |
| 48 | 2-F—C₆H₄ | CH₃ | CH₃ | CH₃ | | | |
| 49 | 2,4-Cl₂—C₆H₃ | CH₃ | CH₃ | CH₃ | | | |
| 50 | 2,4-F₂—C₆H₃ | CH₃ | CH₃ | CH₃ | | | |
| 51 | 4-CH₃—C₆H₄ | CH₃ | CH₃ | CH₃ | | | |
| 52 | 4-CF₃—C₆H₄ | CH₃ | CH₃ | CH₃ | | | |
| 53 | 3-CF₃—C₆H₄ | CH₃ | CH₃ | CH₃ | | | |
| 54 | CH₃ | C₆H₅ | CH₃ | CH₃ | | | |
| 55 | CH₃ | 4Cl—C₆H₄ | CH₃ | CH₃ | | | |
| 56 | CH₃ | 4Br—C₆H₄ | CH₃ | CH₃ | | | |
| 57 | CH₃ | 4F—C₆H₄ | CH₃ | CH₃ | | | |
| 58 | CH₃ | 2F—C₆H₄ | CH₃ | CH₃ | | | |
| 59 | CH₃ | 2,4-Cl₂—C₆H₃ | CH₃ | CH₃ | | | |
| 60 | CH₃ | 2,4-F₂—C₆H₃ | CH₃ | CH₃ | | | |
| 61 | CH₃ | 4-CH₃—C₆H₄ | CH₃ | CH₃ | | | |
| 62 | CH₃ | 4-CF₃—C₆H₄ | CH₃ | CH₃ | | | |
| 63 | CH₃ | 3-CF₃—C₆H₄ | CH₃ | CH₃ | | | |
| 64 | —C(OR³)(OR⁴)—(CH₂)₂ | | CH₃ | CH₃ | | | |
| 65 | —C(OR³)(OR⁴)—(CH₂)₂ | | C₅H₁₁ | C₅H₁₁ | | | |
| 66 | —C(OR³)(OR⁴)—(CH₂)₂ | | —CH₂—C(CH₃)₂ | —CH₂— | | | |
| 67 | —C(OR³)(OR⁴)—(CH₂)₂ | | CH₂ | —CH₂— | | | |
| 68 | —C(OR³)(OR⁴)—(CH₂)₂ | | CH₃ | CH₃ | | | |
| 69 | —C(OR³)(OR⁴)—(CH₂)₂ | | C₅H₁₁ | C₅H₁₁ | | | |
| 70 | —C(OR³)(OR⁴)—(CH₂)₂ | | —CH₂—C(CH₃)₂ | —CH₂— | | | |
| 71 | —C(OR³)(OR⁴)—(CH₂)₂ | | —CH₂ | —CH₂— | | | |
| 72 | —C(OR⁸)(OR⁹)—(CH₂)₄ | | CH₃ | CH₃ | | | |
| 73 | —C(OR⁸)(OR⁹)—(CH₂)₄ | | C₅H₁₁ | C₅H₁₁ | | | |
| 74 | —C(OR⁸)(OR⁹)—(CH₂)₄ | | —CH₂—C(CH₃)₂ | —CH₂— | | | |
| 75 | —C(OR⁸)(OR⁹)—(CH₂)₄ | | —CH₂ | —CH₂— | | | |
| 76 | CH₃ | CH₃ | CH₃ | CH₃ | | | |

We claim:
1. A process for preparing α,α-dialkoxy ketones of the formula I

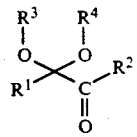

where
R[1] and R[2] are each, independently of one another, hydrogen, $C_1$–$C_{20}$-alkyl, $C_3$–$C_{20}$-cycloalkyl, $C_4$–$C_{30}$-cycloalkylalkyl, $C_9$–$C_{30}$-alkylcycloalkyl, unsubstituted or $C_1$–$C_8$-alkyl-, $C_1$–$C_8$-alkoxy-, halogen-, $C_1$–$C_4$-haloalkyl-, $C_1$–$C_4$-haloalkoxy-, phenyl-, phenoxy-, halophenyl-, halophenoxy- and/or cyano-substituted phenyl or $C_7$–$C_{20}$-phenylalkyl, R[2] can also be

R[3] and R[4] are each, independently of one another, $C_1$–$C_{20}$-alkyl, $C_3$–$C_{20}$-alkyl, $C_3$–$C_{20}$-cycloalkyl, phenyl, 1-naphthyl or 2-naphthyl, $C_7$–$C_{20}$-phenylalkyl, or together are an unsubstituted or $C_1$–$C_4$-alkyl-substituted $C_2$–$C_7$-alkylene chain and is R[1] or together with R[1] is an unsubstituted or $C_1$–$C_4$-alkyl-substituted $C_2$–$C_7$-alkylene chain, which comprises reacting ketones or aldehydes of the formula II

with nitrites of the formula III

where n is 1 or 2, and n is 2 when R[3] and R[4] together are an unsubstituted or $C_1$–$C_4$-alkyl-substituted $C_2$–$C_7$-alkylene chain, with the proviso that the nitrite radicals are located at the termini, in the presence of an acid catalyst selected from the group consisting of HCl, HBr, toluenesulfonic acid, methanesulfonic acid, sulfuric acid, phosphoric acid, acetic acid, trifluoroacetic acid and tetrafluoroboric acid at from 0° to 170° C.

* * * * *